United States Patent [19]

Wheeler

[11] 4,422,870
[45] * Dec. 27, 1983

[54] BIOCIDAL 2-ARYL-1, 3-CYCLOHEXANEDIONE ENOL ESTER COMPOUNDS

[75] Inventor: Thomas N. Wheeler, Charleston, W. Va.

[73] Assignee: Union Carbide Corporation, Danbury, Conn.

[*] Notice: The portion of the term of this patent subsequent to Jun. 24, 1997, has been disclaimed.

[21] Appl. No.: 781,781

[22] Filed: Mar. 28, 1977

[51] Int. Cl.³ ................. A01N 37/02; C07C 69/24

[52] U.S. Cl. .................................. 71/106; 71/98;
560/125; 560/126; 71/103; 560/128; 560/150;
71/105; 560/152; 560/156; 71/107; 560/173;
560/187; 71/111; 560/221; 560/227; 260/399;
560/228; 560/251; 260/402; 560/252; 560/255;
260/404; 568/306; 568/312; 260/404.5;
568/314; 568/316; 260/408; 568/329;
260/410.5; 260/463; 260/465 D; 424/299;
424/304; 424/305; 424/308; 424/309; 424/311;
424/312; 424/314; 560/10; 560/11; 560/18;
560/19; 560/20; 560/73; 560/100; 560/105;
560/107; 560/118; 560/124

[58] Field of Search .............. 560/255, 250, 251, 252,
560/100, 105, 107, 118, 124, 219, 221, 228;
260/410.5, 402, 404, 404.5, 408, 399; 71/98,
103, 106, 107; 424/305, 308, 311, 312, 314

[56] References Cited

U.S. PATENT DOCUMENTS 3,706,784 12/1972 Edwards et al. ............... 560/255
3,712,928 1/1973 Carissimi et al. ............... 560/255
4,209,532 6/1980 Wheeler ........................ 424/331

Primary Examiner—Vivian Garner
Attorney, Agent, or Firm—C. J. Vicari; J. A. Shedden

[57] ABSTRACT

2-Aryl-1, 3-cyclohexanedione enol ester compounds exhibit outstanding miticidal, mite ovicidal and herbicidal activity.

10 Claims, No Drawings

BIOCIDAL 2-ARYL-1, 3-CYCLOHEXANEDIONE ENOL ESTER COMPOUNDS

This invention relates to novel 2-aryl-1,3-cyclohexanedione enol ester compounds and methods of preparing same. This invention is also directed to miticidal, mite ovicidal, post-emergent herbicidal and pre-emergent heribicidal compositions comprising an acceptable carrier and a pesticidally effective amount of a compound of this invention, as well as to a method of controlling mites and plant pests which comprises subjecting the mites, the eggs of mites and the plant pests to a pesticidally effective amount of a compound of this invention.

More particularly, this invention relates to compounds of the formula:

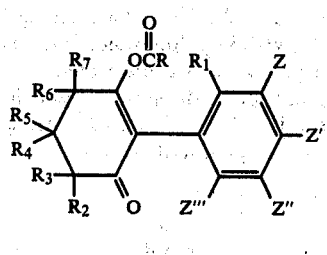

wherein:

$Z$, $Z'$, $Z''$ and $Z'''$ are individually hydrogen, haloalkyl, polyhaloalkyl, halogen, alkyl, alkoxy, cyano, nitro, alkylthio, alkanoyl, amido, amino alkylsulfinyl or alkylsulfonyl;

R is hydrogen, halogen, alkyl, alkenyl, alkynyl, bicycloalkyl, bicycloalkenyl, cycloalkyl, cycloalkenyl, haloalkyl phenyl, phenylalkyl, naphthyl or naphthylalkyl, all of which, other than hydrogen and halogen, may be substituted with one or more alkyl, cyano, nitro, alkoxy, halogen, haloalkyl, alkylthio, alkylsulfinyl, alkylsulfonyl, alkoxyalkyl, alkylthioalkyl, alkylsulfinylalkyl, alkylsulfonylalkyl or dialkylamino substituents;

$R_1$ is alkyl, polyhaloalkyl or haloalkyl or halogen;

$R_2$, $R_3$, $R_4$, $R_5$, $R_6$ and $R_7$ are individually hydrogen or either substituted or unsubstituted alkyl or phenyl, wherein the permissible substituents are one or more alkyl, cyano, halogen, nitro, alkoxy, alkylthio, alkylsulfinyl, alkylsulfonyl or dialkylamino substituents; or any two $R_2$, $R_3$, $R_4$, $R_5$, $R_6$ or $R_7$ substituents together may form an alkylene or alkenylene chain having from 2 to 20 carbon atoms completing a 3, 4, 5, 6 or 7 membered ring structure;

with the proviso that $R_1$, $R_2$, $R_3$, $R_4$, $R_5$, $R_6$, $R_7$, $Z$, $Z'$, $Z''$, and $Z'''$ individually may not include more than ten aliphatic carbon atoms and R may not include more than thirty aliphatic carbon atoms.

The following miticidally, mite ovicidally or herbicidally active compounds are illustrative of compounds within the purview of the above generic formula and which can be conveniently prepared by the process of this invention simply by selecting appropriate reactants for use in the procedures described below:

2-(2'-Chlorophenyl)-3-(7-phenylheptanoyloxy)-5,5-dimethyl-2-cyclohexenone.

2-(2'-chlorophenyl)-3-(2',6'-dichlorohexanoyloxy)-2-cyclohexenone 2-(2'-4'-Dibromophenyl)-3-(hexanoyloxy)-2-cyclohexenone 2-(2'-Chlorophenyl)-3-(2-ethylhexanoyloxy)-2-cyclohexenone 3-(2'-Isopropylphenyl)-4-acetoxy-spiro[5.5]undec-3-en-2-one 2-(2'-Chlorophenyl)-3-benzoyloxy-5,5-dimethyl-2-cyclohexenone 2-(2'-Bromophenyl)-3-(4'-chlorobenzoyloxy)-5,5-dimethyl-2-cyclohexenone 2-(2'-Chlorophenyl)-3-(5'-diethylaminophenylcarbonyloxy)-5,5-dimethyl-2-cyclohexenone 2-(2'-Chlorophenyl)-3-(4'-chlorophenylcarbonyloxy)-5,5-dimethyl-2-cyclohexenone 2-(2'-Chlorophenyl)-3-(4'-methylthiophenylcarbonyloxy)-5,5-dimethyl-2-cyclohexenone 2-(2'-chloro-5'-Nitrophenyl)-3-(4'-dimethylaminophenylcarbonyloxy)-5,5-dimethyl-2-cyclohexenone 2-(2'-Chlorophenyl)-3-(trifluoroacetoxy)-5,5-dimethyl-2-cyclohexenone 2-(2'-Chlorophenyl)-3-(acetoxy)-5,5-dimethyl-2-cyclohexenone.

2-(2'-Trifluoromethyl-4'-nitrophenyl)-3-chlorocarbonyloxy-5,6-dimethyl-2-cyclohexenone 2-(2'-Methyl-4'-nitrophenyl)-3-chlorocarbonyloxy-5,6-dimethyl-2-cyclohexenone 2-(2'Methyl-6'-nitrophenyl)-3-naphthylcarbonyloxy-4,4-diethyl-2-cyclohexenone 2-(2'-4'-Dimethylphenyl)-3-hexanoyloxy-5,5-dimethyl-2-cyclohexenone 2-(2',4'-Dimethylphenyl)-3-(2-ethylhexanoyloxy)-5,5-dimethyl-2-cyclohexenone 2-(2',3'-Dimethylphenyl)-3-stearoyloxy-5,5-dimethyl-2-cyclohexenone 2-(2',5'-Dichlorophenyl)-3-acetoxy-5,5-dimethyl-2-cyclohexenone 2-(2',4'-Dibromophenyl)-3-isobutyryloxy-5,5-dimethyl-2-cyclohexenone 2-(2',6'-Dichlorophenyl)-3-hexanoyloxy-5,5-dimethyl-2-cyclohexenone 2-(2'6'-Dichlorophenyl)-3-(2-ethylhexanoyloxy)-5,6-dimethyl-2-cyclohexenone 2-(2',5'-Dichlorophenyl)-3-stearoyloxy-5,5-dimethyl-2-cyclohexenone 2-(2',3'-Dimethylphenyl)-3-benzoyloxy-5,5-dimethyl-2-cyclohexenone 2-(2',4'-Dimethylphenyl)-3-phenylcarbonyloxy-4,6-dimethyl-2-cyclohexenone 2-(2',4'-Difluorophenyl)-3-(2',4'-dichlorophenylcarbonyloxy)-5,5-dimethyl-2-cyclohexenone 2-(2',4'-Dimethylphenyl)-3-(4'-dimethylaminophenylcarbonyloxy-5,5-dimethyl-2-cyclohexenone 2-(2',4'-Dimethylphenyl)-3-(4'-chlorophenylcarbonyloxy)-5,6-dimethyl-2-cyclohexenone 2-(2',4'-Dimethylphenyl)-3-(2'-ethylthiophenylcarbonyloxy)-5,5-dimethyl-2-cyclohexenone 2-(2',4'-Dimethylphenyl)-3-trifluoroacetoxy-5,5-dimethyl-2-cyclohexenone 2-(2',4'-Dimethylphenyl)-3-dimethylaminoacetoxy-4,5-dimethyl-2-cyclohexenone 2-(2',4'-Dimethylphenyl)-3-methylthioacetoxy-5,5-dimethyl-2-cyclohexenone 2-(2',4'-Dimethylphenyl)-3-methylsulfonylactoxy-5,5-dimethyl-2-cyclohexenone 2-(2',4'-Dimethylphenyl)-3-(2-cyclohexenylcarbonyloxy)-5,5-dimethyl-2-cyclohexenone 2-(2'-Trichloromethyl-4'-nitrophenyl)-3-(2',4-dicyanohexanoyloxy)-4-(2'-chloroethyl)-2-cyclohexenone 2-(2'-Chloro-4'-nitrophenyl)-3-(2'-nitroethanoyloxy)-4,5-diethyl-2-cyclohexenone 2-(2'-Chloro-6'-methoxy-4'-nitrophenyl)-3-pentanoyloxy-6-(2'-cyanoethyl)-2-cyclohexenone 2-(2'-Chlorophenyl)-3-acetoxy-5,5-dimethyl-2-cyclohexenone 2-(2'-Chlorophenyl)-3-(cyclopropylcarbonyloxy)-4,5-dimethyl-2-cyclohexenone 2-(2'-Bromophenyl)-3-(2-ethylhexanoyloxy)-5,6-dimethyl-2-cyclohexenone 2-(2',4',6'-Trimethylphenyl)-3-(4'-cyanobenzoyloxy)-4-methyl-2-cyclohexenone 2-(2'-Methylphenyl)-3-ethanoyloxy-5-(3'-ethylsulfinylphenyl)-2-cyclohexenone 2-(2'-Methylphenyl)-3-(4'-methoxyphenylcarbonyloxy)-5,5-dimethyl-2-cyclohexenone.

2-(2',6'-Dimethylphenyl)-3-(2',4'-dicyanophenylcarbonyloxy)-5,5-dimethyl-2-cyclohexenone 2-(2',4'-Dimethylphenyl)-3-(3'-nitrophenylcarbonyloxy)-5,5-dimethyl-2-cyclohexenone 2-(2'-Methyl-4'-chlorophenyl)-3-(trifluoroacetoxy)-5,5-dimethyl-2-cyclohexenone 2-(2',4'-Dimethylphenyl)-3-(3'-methylthiobenzoyloxy)-5,5-dimethyl-2-cyclohexenone 2-(2'-Methylphenyl)-3-(2'-methylsulfinylbenzoyloxy)-5,5-dimethyl-2-cyclohexenone 2-(2'-Methylphenyl)-3-(4'-methylsulfonylphenylcarbonyloxy)-5,5-dimethyl-2-cyclohexenone 2-(2',4',6'-Trimethylphenyl)-3-cyclopropylcarbonyloxy-5,5-dimethyl-2-cyclohexenone 2-(2',4',6'-Trimethylphenyl)-3-(2-cyclohexenylcarbonyloxy)-5,5-dimethyl-2-cyclohexenone 2-(2'-Methylphenyl)-3-propynoyloxy-5,5-dimethyl-2-cyclohexenone 4-Acetoxy-3-(2',4'-dimethylphenyl)-bicyclo[3.2.1]oct-3-en-2-one 4-(2-Ethylhexanoyloxy)-3-(2'-chlorophenyl)-spiro[5.5]undec-3-en-2-one 2-Hexanoyloxy-3-(2',4'-dichlorophenyl)-bicyclo[4.4.0]-dec-2-en-4-one 3-Isobutyryloxy-4-(4'-chlorophenyl)-2-(2',5'-dimethylphenyl)-2-cyclohexenone All compounds within the purview of the above generic formula exhibit miticidal, mite ovicidal and herbicidal activity to a lesser or greater extent. Some of these compounds exhibit very powerful miticidal, mite ovicidal or herbicidal activity in extremely small dosages while others require larger dosages to be pesticidally effective. In general, the compounds of this invention that exhbiit the highest order of herbicidal activity also exhibit the highest order of miticidal and mite ovicidal activity. Miticidal, mite ovicidal and herbicidal activity is greatest in those compounds having a hydrogen, alkyl, alkoxy, cyano, trihalomethyl or halogen substituent at one of the ortho positions of the 2-phenyl moiety, and an alkyl or halogen group at the other position. Especially active compounds are those in which the ortho substituents are relatively small groups, such as methoxy, ethoxy, methyl, ethyl, hydrogen or halogen.

It has also been found that some of the pesticidal compositions of this invention exhibit excellent fumigant properties. In addition, these compounds are relatively non-toxic to mammals when used in amounts sufficient to kill mites, mite eggs or undesirable plant growth.

Preferred because of their higher level of miticidal, mite ovicidal and herbicidal activity are the 2-aryl-1,3-cyclohexanedione enol ester compounds of this invention in which:

Z, Z', Z" and Z'" are individually hydrogen, alkyl, alkoxy, cyano, halogen or trihalomethyl;

$R_1$ is alkyl or halogen;

$R_2$, $R_3$, $R_4$, $R_5$, $R_6$ and $R_7$ are individually hydrogen or alkyl;

The most active and particularly preferred compounds of this invention are those in which:

Z, Z', Z" and Z'" are individually hydrogen, methyl, methoxy, cyano or halogen;

R is a linear or branched chain alkyl moiety having from 1 to 30 carbon atoms;

$R_1$ is methyl or halogen;

$R_2$, $R_3$, $R_4$, $R_5$, $R_6$ and $R_7$ are individually hydrogen, methyl or ethyl.

The 2-aryl-1,3-cyclohexanedione enol ester compounds of this invention can be conveniently prepared by a variety of methods. Two preferred methods which utilize the 2-aryl-1,3-cyclohexanedione parent compound as the precursor are illustrated by the general reaction schemes set forth below in which R, $R_1$, $R_2$, $R_3$, $R_4$, $R_5$, $R_6$, $R_7$, Z, Z', Z" and Z'" are as described above and X is halogen, hydroxyl or $$-\overset{O}{\underset{\|}{O}}CR,$$

except as noted:

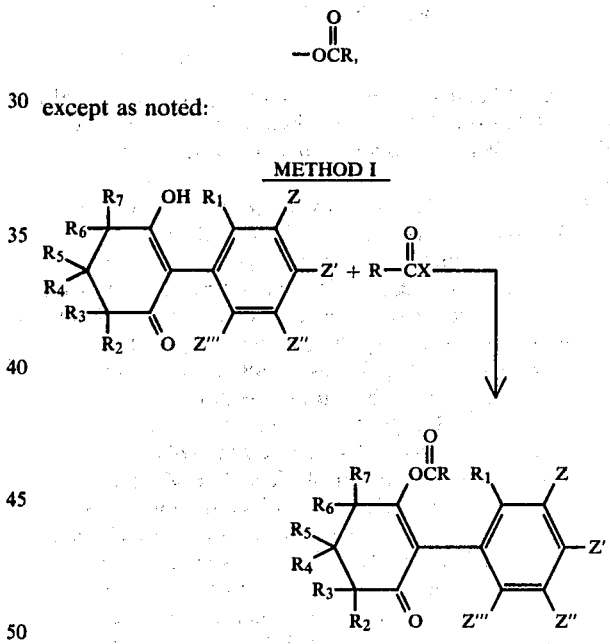

In the reactions illustrated in METHOD I one equivalent of the corresponding 2-arylcyclohexane-1,3-dione compound is reacted with an appropriately substituted acid, acid halide or anhydride compound in the presence of at least one equivalent of an acid acceptor, preferably in an inert solvent.

The acid acceptor utilized in the reactions of METHOD I can be either an organic or an inorganic base. Illustrative of organic bases that are useful as acid acceptors in the conduct of these reactions can mention tertiary amines, such as triethylamine, pyridine, trimethylamine or 1,4-diazobicyclo[2.2.2] octane; or alkali metal alkoxides, as for example, sodium methoxide, sodium ethoxide or the like. Bases such as sodium carbonate, sodium hydroxide or potassium hydroxide are illustrative of inorganic bases that are useful as acid acceptors. Preferred organic acid acceptors are tertiary amines such as triethylamine, pyridine or trimethylamine.

In general, any organic solvent that is inert to the reactants or reaction conditions may be employed in the reaction of METHODS I. Illustrative of organic solvents which are generally suitable for use in the conduct of these reactions are saturated, unsaturated and aromatic hydrocarbons, e.g. hexane, cyclohexane, octane, cyclohexene, dodecane, naphtha, Decalin, kerosene, cycloheptane, benzene, toluene, xylene, naphthalene or the like; ethers such as dioxane, tetrahydrofuran, diethyl ether, tetrahydropyran, 1,2-dimethoxybenzene, 1,2-diethylbenzene, the dialkyl ethers of ethylene glycol, of propylene glycol or chlorinated aliphatic hydrocarbons as for example, chloroform, dichloromethane, methylene dichloride, 1,1-dichloroethane, carbon tetrachloride or the like.

In a preferred embodiment, the reactions illustrated in METHOD I are conducted in a solvent that also functions as the acid acceptor. Illustrative of such multifunctional solvents are N,N-dimethylaniline, pyridine, alpha-picoline, any lutidine, collodine or any like aromatic or heterocyclic tertiary amine compound.

The reactions illustrated in METHOD I are neither temperature nor pressure sensitive and can be conducted over a broad temperature and pressure range to yield the desired product. Preferably, these reactions are conducted at a temperature of from −40° C. to about 120° C. and at atmospheric or autogeneous pressure.

The acid halide, acid and anhydride compounds utilized as reactants in the procedure described in METHODS I above are known classes of compounds that can either be obtained from commercial sources or prepared in accordance with conventional methods known to those skilled in the art.

The 2-aryl-1,3-cyclohexanedione compounds utilized as reactants in the procedure of METHOD I can be conveniently prepared in accordance with a number of synthetic procedures. For example, 2-aryl-1,3-cyclohexanedione compounds in which Z''' is hydrogen can be prepared by heating the corresponding 6-aryl-5-ketopolyalkyl hexanoic acid compound with sulfuric acid or alternatively by treating the corresponding 6-aryl-5-ketopolyalkylhexanoic acid ester with base. The 2-arylcyclohexane-1,3-dione compounds in which at least one ortho substituent is alkyl and the other ortho substituent is other than hydrogen, can be conveniently prepared by the benzophenone sensitized photolysis of the corresponding 2-diazocyclohexane-1,3-dione compound in an appropriately substituted aromatic solvent. The remaining 2-aryl-1,3-cyclohexanedione precursors can be conveniently prepared by reacting the corresponding 1,3-cyclohexanedione compound with an appropriately substituted halobenzene compound. These synthetic procedures are described in more detail in my copending U.S. patent application Ser. No. 781,985 filed Mar. 28, 1977 now U.S. Pat. No. 4,209,532, entitled BIOCIDAL 2-ARYL-1,3-CYCLOHEXANEDIONE COMPOUNDS, filed concurrently herewith.

The following specific examples are presented to more particularly illustrate this invention.

EXAMPLE I

Preparation of 3-(2-Ethylhexanoyloxy)-2-(2'-chlorophenyl)-5,5-dimethyl-2-cyclohexenone A solution of 1.009 (3.99 mmol) of 2-(2'-chlorophenyl)-5,5-dimethyl-1,3-cyclohexanedione and 0.03 g (8.0 mmol) of pyridine was cooled in an ice bath and stirred under $N_2$. The 2-ethylhexanoyl chloride (0.69 g, 4.25 mmol) was added, the mixture was then allowed to warmed to room temperature, stirred at room temperature for one hour and refluxed for one hour. The solvent was removed under reduced pressure and the residue taken up in ether and water. The ether was washed three times with 0.25 N NaOH, three times with 10% HCl and with water. The ether was dried over anhydrous $MgSO_4$ and decanted to give 1.23 g (82%) of 3-(2'-ethylhexanoyloxy)-2-(2'-chlorophenyl)-5,5-dimethyl-2-cyclohexanone as a clear colorless oil which was homogeneous by thin layer chromatography.

Calculated for $C_{22}H_{29}ClO_3$: C, 70.10; H, 7.76; Found: C, 70.09; H, 7.86

EXAMPLE II

Preparation of 3-(2'-Ethylhexanoyloxy)-2-(2',4'-dichlorophenyl)-5,5-dimethyl-2-cyclohexenone A solution of 1.76 g (7.02 mmol) of 2-(2',4'-dichlorophenyl)-5,5-dimethyl-1,3-cyclohexanedione in 10 ml of chloroform was cooled in ice and 1.11 g (14.04 mmol) of pyridine added followed by 1.21 g (7.47 mmol) of 2-ethylhexanoyl chloride. The mixture was stirred for 2 hrs. at room temperature and then refluxed for 12 hrs.

The reaction mixture was worked up exactly as described for Example I above to give 2.09 g of a yellow oil. This material was chromatographed using low pressure liquid chromatography on silica gel with a hexane-ethyl acetate gradient to give 1.15 g (41%) of 3-(2'-ethylhexanoyloxy)-2-(2',4'-dichlorophenyl)-5,5-dimethyl-2-cyclohexenone as a clear, colorless oil. The thin layer chromatogram (80:20 hexane-ethyl acetate) of this material showed one spot at Rf=0.46.

Calculated for $C_{22}H_{28}Cl_2O_3$: C, 64.23; H, 6.86; Found: C, 64.44; H, 6.80

EXAMPLE III

Preparation of 3-hexanoyloxy-5,5-dimethyl-2-(2',4'-dimethylphenyl)-2-cyclohexenone A solution of 1.50 g (6.14 mmol) of 2-(2',4'-dimethylphenyl)-5,5-dimethyl-1,3-cyclohexanedione in 10 ml of chloroform was cooled in ice and 1.94 g (24.56 mmol) of pyridine added followed by 1.64 g (12.28 mmol) of hexanoyl chloride. The mixture was stirred for 2 hrs. at room temperature, then refluxed for 5 hrs.

The reaction mixture was cooled to room temperature and taken up in 150 ml of ether. The ether was washed three times with 50 ml of 0.25 N NaOH, twice with 50 ml portions of ice cold 6 N HCl, and twice with water. The ether was dried over anhydrous ($MgSO_4$) and removed under reduced pressure to leave 0.98 g (47% yield) 3-hexanoyloxy-5,5-dimethyl-2-(2',4'-dimethylphenyl)-2-cyclohexenone as a clear, colorless oil. This oil showed one spot on a thin layer chromatogram (70:30 hexane-ethyl acetate) at Rf=0.49.

Calculated for $C_{22}H_{30}O_3$: C, 77.15; H, 8.83; Found: C, 77.25; H, 8.92

EXAMPLE IV

Preparation of 3-(2-Ethylhexanoyloxy)-5,5-dimethyl-2(2',4'-dimethylphenyl)-2-cyclohexenone A solution of 1.50 g (6.14 mmol) of 2-(2',4'-dimethylphenyl)-5,5-dimethyl-1,3-cyclohexanedione in 10 ml of chloroform was cooled in ice and 1.94 g (24.56 mmol) of pyridine added followed by 2.00 g (12.28 mmol) of 2-ethylhexanoyl chloride. The mixture was stirred for 2 hrs. at room temperature, then refluxed for 12 hrs. The mixture was worked up exactly as described in Example I above to give 1.58 g of a slightly yellow, viscous oil. This material was chromatographed through 75 g of silica gel (0.063-0.2 mm) using a gradient ranging from 98:2 to 90:10 hexane-ethyl acetate. The chromatography gave 1.15 g (51%) of 3-(2-ethylhexanoyloxy)-5,5-dimethyl-2-(2',4'-dimethylphenyl)-2-cyclohexenone as a clear colorless oil which showed one spot on a thin layer chromatogram (70:30 hexane-ethyl acetate) at Rf=0.52.

Calculated for: $C_{24}H_{34}O_3$: C, 77.80; H, 9.25; Found: C, 77.34; H, 9.48

EXAMPLE V

Preparation of 3-Hexanoyloxy-2-(2',4'-dichlorophenyl)-5,5-dimethyl-2-cyclohexenone A solution of 2.00 g (8.00 mmol) of 2-(2',4'-dichlorophenyl)-5,5-dimethyl-1,3-cyclohexenedione in 10 ml of chloroform was cooled in ice and 1.26 g (16.00 mmol) of pyridine was added followed by 1.14 g (8.50 mmol) of hexanoyl chloride. The mixture was stirred for 2 hrs. at room temperature and refluxed for 12 hrs.

The reaction mixture was worked up exactly as described for Example I above to give 1.94 g of a slightly yellow oil. This material was chromatographed using a low pressure liquid chromatography system and a hexane-ethyl acetate gradient. Work-up of the chromatography gave 1.55 g (51% yield) of 3-hexanoyloxy-2-(2',4'-dichlorophenyl)-5,5-dimethyl-2-cyclohexenone as a clear, colorless oil which on a thin layer chromatogram (80:20 hexane-ethyl acetate) showed one spot at Rf=0.27.

Calculated for: $C_{20}H_{24}Cl_2O_3$: C, 62.67; H, 6.31; Found: C, 62.83; H, 6.32

EXAMPLE VI

Preparation of 3-(2-Ethylhexanoyloxy)-5,5-dimethyl-2-(2',5'-dimethylphenyl)-2-cyclohexenone A suspension of 1.50 g (6.14 mmol) of 2-(2',5'-dimethylphenyl)-5,5-dimethyl-1,3-cyclohexanedione in 15 ml of dry benzene was prepared and 0.49 g (7.37 mmol) of 85% powdered potassium hydroxide was added, followed by 1 drop of dicyclohexyl-18-crown-6-ether. After stirring for 30 minutes, 1.20 g (7.37 mmol) of 2-ethylhexanoyl chloride was added, and the reaction mixture refluxed for 12 hrs. The reaction mixture was cooled to room temperature, taken up in 150 ml ether and 50 ml of water, washed three times with 0.25 N NaOH, two times with water, two times with 6 N HCl, and once more with water. The ether solution was dried and stripped to leave 2.10 g (92% yield) of 3-(2-ethylhexanoyloxy)-5,5-dimethyl-2-(2',5'-dimethylphenyl)-2-cyclohexenone as a clear, colorless oil.

Calculated for: $C_{24}H_{34}O_3$: C, 77.80; H, 9.25; Found: C, 77.46, H, 8.98

EXAMPLE VII

Preparation of 2-(2',4'-Dimethylphenyl)-1,3-cyclohexanedione

A 500 ml 3-neck round bottom flask was equipped with a mechanical stirrer, addition funnel, and reflux condenser. The glassware was dried thoroughly and the flask charged with 4.62 g (0.096 g-atom) of 50% sodium hydride in mineral oil. The oil was washed off the NaH using toluene, and then 100 ml of toluene added. The mixture was warmed to 65° C. and 12.62 g (0.0481 mol) ethyl 6-(2',4' dimethylphenyl)-5-ketohexanoate added, dropwise, over a 2 hr. period. The mixture was maintained at 65° C. for 12 hrs., then carefully quenched with 25 ml of ice water. The reaction mixture was diluted with 250 ml of water and extracted twice with 150 ml of ether. The aqueous base solution was acidified to pH=3 with 6 N HCl, and extracted twice with 150 ml of methylene chloride. The methylene chloride was washed with water, dried over anhydrous $MgSO_4$ and stripped to give 5.88 g of a semi-solid. This was recrystallized from ethyl acetate to give 5.10 g (49%) of 2-(2',4'-dimethylphenyl)-1,3-cyclohexanedione as a white, crystalline solid, m.p. 143°-145° C.

Calculated for: $C_{14}H_{16}O_2$: C, 77.75; H, 7.46; Found: C, 76.99; H, 7.46

EXAMPLE VIII

Preparation of 2-(2'-Chlorophenyl)-1,3-cyclohexanedione

A 500 ml one-neck round bottom flask was charged with 10.0 g (0.0416 mol) of 6-(2'-chlorophenyl-5-ketohexanoic acid and 100 ml of 72% sulfuric acid. The reaction mixture was stirred and heated to 120° C. for 5½ hrs. (oil bath) then poured into 600 ml of ice water. A tacky, white solid formed, and this was extracted into 300 ml of methylene chloride. The $CH_2Cl_2$ solution was washed six times with water, dried over anhydrous $MgSO_4$, and stripped to leave 8.87 g of a tacky, white solid. This material was recrystallized from ethyl acetate to give 5.85 g (63%) of 2-(2'-Chlorophenyl)-1,3-cyclohexanedione as a white, crystalline solid, m.p. 148.5°-149° C.

Calculated for: $C_{12}H_{11}ClO_2$: C, 64,73; H, 4.98; Found: C, 64.49; H, 4.89

EXAMPLE IX

Preparation of 2-(2'-Chloro-4'-nitrophenyl)-5,5-dimethyl-1,3-cyclohexanedione A solution containing 42.05 g (0.300 mol) of 5, 5-dimethyl-1,3-cyclohexanedione and 100 g (0.718 g-atom) of anhydrous potassium carbonate in 300 ml of dry dimethylformamide was heated to 75° C. under nitrogen and stirred for one hour. The 3,4-dichloronitrobenzene, 57.60 g (0.300 mol) was dissolved in 100 ml dimethylformamide and added dropwise to the reaction mixture while stirring and maintaining the temperature of the reaction mixture at 75° C. A deep red-colored solution formed, and when the addition was complete the reaction temperature was raised to 100° C. and held at this temperature for 3 hours. Most of the dimethylformamide was removed by vacuum distillation. The residue was poured into 2 l of ice water and extracted three times with 500 ml of benzene. Nitrogen was then passed through the aqueous solution while warming to remove dissolved benzene. The aqueous solution was cooled in an ice bath and acidified to give a tacky precipitate, which, upon warming solidified and was collected by suction filtration. The reaction product was recrystallized from acetone to give 31.7 g (36%) of 2-(2'-Chloro-4'-nitrophenyl)-5,5-dimethyl-1,3-cyclohexanedione as a white powder, m.p. 250°–253° C.

Calculated for: $C_{14}H_{14}ClNO_4 \cdot \frac{1}{2}H_2O$: C, 55.18; H, 4.96; N, 4.60; Found: C, 55.53; H, 4.73; N, 5.09

EXAMPLE X

Preparation of 2-(2'-Chloro-4'-aminophenyl)-5,5-dimethyl-1,3-cyclohexanedione

A solution of 20.0 g (0.067 mol) of 2-(2'-chloro-4'-nitrophenyl)-5,5-dimethyl-1, 3-cyclohexanedione in 150 ml of concentrated ammonium hydroxide and 150 ml of ethanol was stirred at room temperature while passing hydrogen sulfide gas through the solution at such a rate that all of the $H_2S$ was absorbed. When the solution was saturated with $H_2S$, the temperature was raised to the reflux point and $H_2S$ continuously passed slowly through the refluxing solution for 24 hours. The reaction mixture was filtered to remove sulfur, and the filtrate evaporated under reduced pressure. To the residue was added 300 ml of 0.25 N NaOH, and the solution filtered once more. The filtrate ws cooled and carefully acidified to pH=4 with 6 N HCl. A white solid formed which was collected by suction filtration to give 13.3 g (74%) of 2-(2'-Chloro-4'-aminophenyl)-5,5-dimethyl-1, 3-cyclohexanedione, m.p. 218°–219° C.

Calculated for: $C_{14}H_{16}Cl\ NO_2 \cdot \frac{1}{2}H_2O$: C, 61.20; H, 6.24; N, 5.10; Found: C, 60.44; H, 5.83; N, 5.32

EXAMPLE XI

Preparation of 2-(2'-Chlorophenyl)-5,5-dimethyl-1,3-cyclohexanedione

The 2-(2'-chloro-4'-aminophenyl)-5,5-dimethyl-1, 3-cyclohexanedione (9.66 g. 0.0364 mol) was added to 7.0 ml of concentrated HCl in 150 ml of water, and the mixture stirred and heated almost to boiling. An additional 15.0 ml of HCl was added and the mixture cooled to 0°–5° C. A solution of 3.22 g (0.0467 mol) of sodium nitrite in 9.0 ml of water was added dropwise while the reaction mixture was stirred and maintained at 0°–5° C. When addition of the sodium nitrite solution was complete, the reaction mixture was stirred at 0°–5° C. for one hour.

The diazonium salt solution prepared above was added in portions to 161 ml of 50% hypophosphorous acid at 0° C., with stirring and cooling. The reaction mixture was stirred for 12 hours and filtered to give 8.55 g of a tan solid. This material was chromatographed through 250 g of Woelm silica gel (0.063–0.2 mm) eluting with a gradient from pure benzene to 70:30 benzene-ethyl acetate. A total of 7.12 g of product was obtained from the chromatography and recrystallized from benzene-ethyl acetate to give 6.85 g (75%) of 2-(2-Chlorophenyl)-5,5-dimethyl-1, 3-cyclohexanedione as white crystals, m.p. 191°–192° C.

Calculated for: $C_{14}H_{15}ClO_2$: C, 67.07; H, 6.03; Found: C, 67.04; H, 6.00

EXAMPLE XII

Preparation of 2-(2',4'-6'-Trimethylphenyl)-cyclohexane-1, 3-dione

A solution of 5.00 g (0.036 mol) of 2-diazocyclohexane-1, 3 -dione in 500 ml of mesitylene (dry, distilled) containing 32.8 g (0.18 mol) benzophenone was degassed with nitrogen for one hour, and irradiated with a 200 watt Hanovia immersion lamp through a borosilicate glass filter, until the complete disappearance of the diazo band (4.68μ) in the infrared was observed. The reaction was also monitored by thin layer chromatography (90:10 ethyl acetate-benzene) and irradiation continued until no diazoketone at $R_f=0.31$ could be seen. The irradiation required 11 hours. The mesitylene was extracted with 0.25 N sodium hydroxide until a small aliquot showed no cloudiness upon acidification. The combined base extracts were washed twice with 200 ml of ether, and acidified (pH=5) with 1 N HCl. The aqueous solution was extracted three times with 75 ml portions of chloroform, dried over anhydrous $MgSO_4$, and the solvent stripped to give 5.06 g of a tan solid.

This solid was chromatographed through 250 g of silica gel (0.063–0.2 mm) eluting with a gradient from pure benzene to 80:20 benzene-ethyl acetate. A total of 2.60 g (31%) of a white solid (homogeneous by thin layer chromatography) was obtained and recrystallized from diisopropyl ether to give 1.96 g of 2-(2',4',6'-trimethylphenyl)-1,3-cyclohexanedione as white crystals, mp 196°–198° C.

Calculated for: $C_{15}H_{18}O_2$: C, 78.23; H, 7.88; Found: C, 77.94; H, 8.20

Selected 2-aryl-1,3-cyclohexanedione enol ester compounds, representative of those useful in accordance with this invention were tested with respect to their miticidal, mite ovicidal and pre-emergent and post-emergent herbicial activity.

Suspensions of the test compounds were prepared by dissolving one gram of compound in 50 milliliters of acetone in which had been dissolved 0.1 gram (10 percent of the weight of compound) of an alkylphenoxyethanol surfactant, as an emulsifying or dispersing agent. The resulting solution was mixed into 160 milliliters of water to give roughly 200 milliliters of a suspension containing the compound in finely divided form. The thus prepared stock suspension contained 0.5 percent by weight of compound. The test concentrations employed in the tests described hereinbelow were obtained by diluting the stock suspension with water. The test procedures were as follows:

MITE FOLIAGE SPRAY TEST

Adults and nymphal stages of the two-spotted mite (tetranychus urticae (Koch)), reared on Tendergreen bean plants at 80±5° F. and 50±5° percent relative humidity, were the test organisms. Infested leaves from a stock culture were placed on the primary leaves of two bean plants six to eight inches in height, growing in a two-and-a-half inch clay pot. 150–200 Mites, a sufficient number for testing, transferred from the excised leaves to the fresh plants in a period of twenty-four hours. Following the twenty-four hour transfer period, the excised leaves were removed from the infested plants. The test compounds were formulated by diluting the stock suspension with water to provide suspensions containing the desired amount of test compound per million parts of final formulation. The potted plants (one pot per compound) were placed on a revolving turntable and sprayed with 100–110 milliliters of test compound formulation by use of a DeVilbis spray gun set at 40 psi. air pressure. This application, which lasted 30 seconds, was sufficient to wet the plants to run-off. As a control, 100–110 milliliters of a water solution containing acetone and emulsifier in the same concentrations as the test compound formulation, but containing no test compounds, were also sprayed on infested plants. The sprayed plants were held at 80±5° F. and 50±5 percent relative humidity for four days, after which, a mortality count of motile forms were made. Microscopic examination for motile forms were made on the leaves of the test plants. Any individual which was capable of locomotion upon prodding was considered living.

Mite Ovicide Test

The test organism was the egg of the two-spotted mite (Tetranychus urticae (Koch)), as obtained from adults reared on Tendergreen bean plants under controlled conditions of 80±5° F. and 50±5 percent relative humidity. Heavily infested leaves from a stock culture were placed on the primary leaves of two bean plants six to eight inches in height, growing in a two-and-a-half inch clay pot. Females were allowed to oviposit for period of 48 hours and then the leaves of the infested plants were dipped in a solution containing 800 parts of tetraethyl pyrophosphate per million parts of water in order to destroy the reproductory forms and thus prevent further egg laying. This solution of tetraethyl pyrophosphate does not affect the viability of the eggs. The plants were allowed to dry thoroughly. The test compounds were formulated by diluting the stock suspension with water to give a suspension containing varying amounts of test compound per million parts of final formulation. The potted plants (one pot per compound) were placed on a revolving turntable and sprayed with 110–110 milliliters of test compound formulation by use of a DeVilbis spray gun set at 40 psig. air pressure. This application, which lasted 30 seconds, was sufficient to wet the plants to run-off. As a control, 100–110 milliliters of a water solution containing acetone and emulsifier in the same concentrations as the test compound formulation, but containing no test compound, were also sprayed on plants infested with eggs. The sprayed plants were held at 80±5° F. and 50±5 percent relative humidity for four days, after which a microscopic examination was made of unhatched (dead) and hatched (living) eggs.

In these tests the pesticidal activity of the compounds against mites and mite eggs was rated as follows:
A=Excellent Control
B=Partial Control
C=No Control Preliminary Herbicide Seed Germination Test The following seeds were used in this test:

| | |
|---|---|
| Perennial rye grass | Solium perenne |
| Crabgrass | Digitaria sanguinalis |
| Red root pigweed | Amaranthus retroflexus |
| Mustard | Brassica pincea var. foliosa (Florida broadleaf) |

Two seed-soil mixtures were prepared as follows:

| | |
|---|---|
| Mixture I | 196 cc. Rye grass seed |
| | 75 cc. Mustard seed |
| | 18,000 cc. Sifted, fairly dry soil |
| Mixture II | 99 cc. Crabgrass seed |
| | 33 cc. Amaranthus |
| | 18,000 cc. Sifted, fairly dry soil |

Each of above mixtures was rolled separately in 5 gallon containers for approximately one-half hour on a ball mill to insure uniform mixing of seeds and soil. For each compound four 3-inch pots were filled with soil to within 1½ inches of the top of the pots. To 2 of these pots was added 70 cc. of Mixture I. To the remaining 2 pots was added 70 cc. of Mixture II. The seed-soil mixture was tamped firmly, and the pots were removed to the greenhouse and watered lightly. About 2 hours after planting, 25 milliliters of the test formulation were added to each of 2 pots for each soil-seed mixture; i.e., one replicate of each seed mixture per concentration. An equal volume of a water solution containing acetone and an emulsifier in the same concentration as the herbicidal mixture but without the candidate herbicide was also added to each of the soil-seed mixtures. These pots are used as check or control units. The test compounds are formulated by standard procedure of solution in acetone, addition of an emulsifier, and dilution with water. Tests were conducted on all compositions at low concentration (100 ppm.). Certain compositions were also tested at high concentration (1000 ppm). The pots were held in the greenhouse and watered lightly until results were taken. Ten to twelve days after application of chemical, injury is noted for each species by comparing treated vs. untreated pots. Ratings are made at both the high and the low concentrations (1000 ppm and 100 ppm) according to the following designations:
5=no seedlings emerged
4=few seedlings emerged and/or very severe stunting
3=moderate reduction in stand and/or moderate stunting
2=very slight reduction in stand and/or slight stunting
1=no injury; seedlings appear no different with respect to stand or growth than untreated controls

POST-EMERGENT HERBICIDAL TEST

Experiments were also conducted to determine the phytotoxicity of representative compositions with respect to healthy fresh plants. Solutions of the compounds were prepared as described above to provide a concentration of 2500 parts per million of the test compound. The test plants were sprayed in accordance with the procedure described above for the Mite Foliage Spray Test so as to deliver approximately 100 milliliters of test solution to the leaves of each plant tested. The sprayed plants and controls were set aside for approximately one hour to allow the solutions to dry and were then placed in the greenhouse. After ten days the plants were visually inspected to determine the extent of foliage injury. A rating of 1 indicates no perceptible injury; 5 indicates the plant was dead and ratings of 2, 3 and 4 inidcate intermediate degrees of injury based upon the number and extent to which leaves were injured.

The results of these experiments are summarized and set forth in Table I, below.

TABLE I

PHYSICAL PROPERTIES AND BIOLOGICAL ACTIVITY OF 2-ARYL-1,3-CYCLOHEXANEDIONE ENOL ESTER COMPOUNDS

| STRUCTURE | MP °C. or IR | BIOLOGICAL ACTIVITY | | | | | | | | | |
|---|---|---|---|---|---|---|---|---|---|---|---|
| | | Miticidal | | Post-emergent Herbicidal | | | | | Pre-emergent Herbicidal | | |
| | | Adult | Egg | Bean | Corn | Tomato | Cotton | Soybean | Rye | Crabgrass | Amaranthus | Mustard |
| (cyclopropyl)-(H$_2$C)$_6$-CO-O-[2,4-Cl$_2$-phenyl-5,5-dimethylcyclohexenone] | λmax (μ): 5.75 (ester C=O); 6.05 (keto C=O) | A | A | 1 | 5 | 2 | 2 | 2 | 5 | 5 | 4 | 4 |
| (H$_3$C)$_2$HC(H$_2$C)$_6$-CO-O-[...] | λmax (μ): 5.70 (ester C=O); 5.75, 6.0 (keto C=O) | A | A | 1 | 4 | 1 | 1 | 1 | 5 | 5 | 3 | 3 |
| φ-(H$_2$C)$_6$-CO-O-[...] | λmax (μ): 5.75 (ester C=O); 6.0, 6.05 (keto C=O) | A | A | 1 | 4 | 1 | 1 | 1 | 5 | 5 | 1 | 3 |
| H$_3$C-(H$_2$C)$_{16}$-CO-O-[...] | λmax (μ) 5.75 (ester C=O); 6.05 (keto C=O) | A | A | 1 | 1 | 1 | 1 | 1 | 4 | 5 | 2 | 3 |
| (cyclopropyl)-CO-O-[...] | 76.5–78 | A | A | 1 | 5 | 2 | 2 | 3 | 5 | 5 | 4 | 4 |
| (H$_3$C)$_3$CCO-O-[...] | 91–93 | A | A | 1 | 3 | 1 | 1 | 1 | 5 | 5 | 3 | 3 |
| H$_3$C-(H$_2$C)$_4$-CO-O-[...] | λmax (μ): 5.70 (ester C=O); 6.0, 6.05 (keto C=O) | A | A | 2 | 4 | 1 | 2 | 3 | 5 | 5 | 3 | 4 |

TABLE I-continued

PHYSICAL PROPERTIES AND BIOLOGICAL ACTIVITY OF 2-ARYL-1,3-CYCLOHEXANEDIONE ENOL ESTER COMPOUNDS

| STRUCTURE | MP °C. or IR | Miticidal Adult | Miticidal Egg | Post-emergent Herbicidal Bean | Post-emergent Herbicidal Corn | Post-emergent Herbicidal Tomato | Post-emergent Herbicidal Cotton | Post-emergent Herbicidal Soybean | Pre-emergent Herbicidal Rye | Pre-emergent Herbicidal Crabgrass | Pre-emergent Herbicidal Amaranthus | Pre-emergent Herbicidal Mustard |
|---|---|---|---|---|---|---|---|---|---|---|---|---|
| 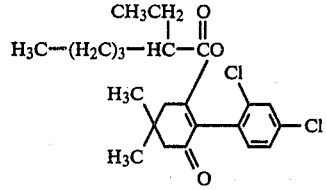 | λmax (μ): 5.70 (ester C=O); 6.0, 6.05 (keto C=O) | A | A | 1 | 4 | 1 | 1 | 1 | 1 | 1 | 1 | 1 |
| 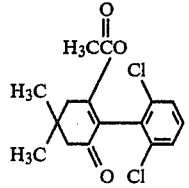 | 41–42.5 | A | A | 2 | 2 | 2 | 2 | 3 | 5 | 5 | 2 | 2 |
| 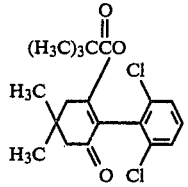 | 84–85 | A | A | 2 | 2 | 2 | 2 | 1 | 5 | 5 | 1 | 2 |
| 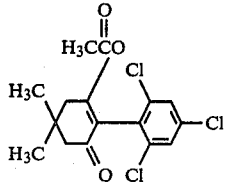 | 99.5–101 | A | A | 1 | 3 | 1 | 1 | 1 | 2 | 2 | 1 | 1 |
| 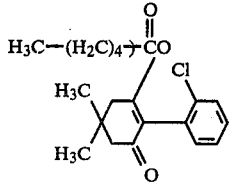 | λmax (μ): 5.72 (ester C=O); 6.0, 6.05 (keto C=O) | A | A | 2 | 5 | 2 | 2 | 2 | 5 | 5 | 4 | 3 |
| 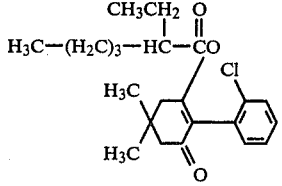 | λmax (μ): 5.70 (ester C=O); 5.95, 6.0 (keto C=O) | A | A | 2 | 5 | 1 | 1 | 1 | 2 | 2 | 1 | 1 |
| 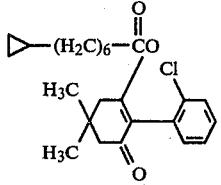 | λmax (μ): 5.68 (ester C=O); 5.95, 6.0 (keto C=O) | A | A | 1 | 3 | 2 | 2 | 2 | 5 | 5 | 4 | 3 |

TABLE I-continued
PHYSICAL PROPERTIES AND BIOLOGICAL ACTIVITY OF 2-ARYL-1,3-CYCLOHEXANEDIONE ENOL ESTER COMPOUNDS

| STRUCTURE | MP °C. or IR | BIOLOGICAL ACTIVITY | | | | | | | | | |
|---|---|---|---|---|---|---|---|---|---|---|---|
| | | Miticidal | | Post-emergent Herbicidal | | | | | Pre-emergent Herbicidal | | | |
| | | Adult | Egg | Bean | Corn | To-mato | Cot-ton | Soy-bean | Rye | Crab-grass | Amar-anthus | Mus-tard |
| (H3C)2HC(H2C)6—CO... 2-Cl-phenyl, gem-diMe cyclohexanedione | λmax (μ): 5.75 (ester C=O); 6.0, 6.05 (keto C=O) | A | A | 1 | 5 | 1 | 1 | 1 | 5 | 5 | 3 | 3 |
| φ-(H2C)6—CO... 2-Cl-phenyl, gem-diMe cyclohexanedione | λmax (μ); 5.75 (ester C=O); 6.0, 6.05 (Keto C=O) | A | A | 1 | 4 | 1 | 1 | 1 | 4 | 5 | 1 | 2 |
| H3C—(H2C)16—CO... 2-Cl-phenyl, gem-diMe cyclohexanedione | 47-49 | A | A | 1 | 1 | 1 | 1 | 1 | 3 | 4 | 2 | 2 |
| H3CCO... 2,4-diCl-phenyl, gem-diMe cyclohexanedione | 92.5-94 | A | A | 1 | 3 | 1 | 1 | 1 | 5 | 5 | 3 | 3 |
| (H3C)2HCCO... 2,4-diCl-phenyl, gem-diMe cyclohexanedione | 65.5-66.5 | A | A | 2 | 5 | 2 | 2 | 3 | 5 | 5 | 3 | 4 |
| H3CCO... 2-Cl-phenyl, gem-diMe cyclohexanedione | λmax (μ); 5.70 (ester C=O); 6.05 (keto; C=O) | A | A | 2 | 4 | 2 | 2 | 3 | 5 | 5 | 3 | 3 |
| (H3C)2HCCO... 2-Cl-phenyl, gem-diMe cyclohexanedione | λmax (μ); 5.73 (ester C=O); 6.05 (keto C=O) | A | A | 1 | 4 | 2 | 2 | 3 | 5 | 5 | 4 | 4 |

TABLE I-continued
PHYSICAL PROPERTIES AND BIOLOGICAL ACTIVITY OF 2-ARYL-1,3-CYCLOHEXANEDIONE ENOL ESTER COMPOUNDS
| STRUCTURE | MP °C. or IR | BIOLOGICAL ACTIVITY | | | | | | | | | |
|---|---|---|---|---|---|---|---|---|---|---|---|
| | | Miticidal | | Post-emergent Herbicidal | | | | | Pre-emergent Herbicidal | | | |
| | | Adult | Egg | Bean | Corn | Tomato | Cotton | Soybean | Rye | Crabgrass | Amaranthus | Mustard |
| 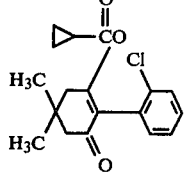 | 77–78 | A | A | 2 | 3 | 2 | 2 | 2 | 5 | 5 | 5 | 3 |
| 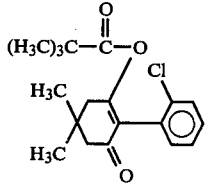 | 86–87 | A | A | 2 | 2 | 2 | 2 | 1 | 5 | 5 | 1 | 3 |
| 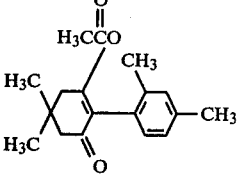 | λmax (μ); 5.75 (ester C=O); 6.05, 6.10 (keto C=O) | A | A | 2 | 5 | 2 | 2 | 3 | 5 | 5 | 5 | 3 |
| 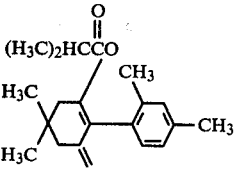 | 238–240 | A | A | 2 | 5 | 2 | 2 | 3 | 5 | 5 | 4 | 5 |
| 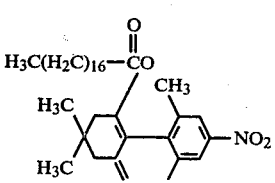 | 42–44 | C | C | 1 | 1 | 1 | 1 | 1 | 1 | 1 | 1 | 1 |
| 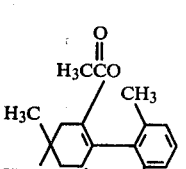 | 79.5–81 | A | A | 1 | 3 | 2 | 2 | 2 | 4 | 4 | 4 | 3 |
| 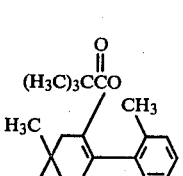 | 101.5–103 | A | A | 1 | 1 | 1 | 1 | 1 | 5 | 5 | 2 | 2 |

TABLE I-continued
PHYSICAL PROPERTIES AND BIOLOGICAL ACTIVITY OF 2-ARYL-1,3-CYCLOHEXANEDIONE ENOL ESTER COMPOUNDS

| STRUCTURE | MP °C. or IR | Miticidal Adult | Miticidal Egg | Post-emergent Herbicidal Bean | Corn | Tomato | Cotton | Soybean | Pre-emergent Herbicidal Rye | Crabgrass | Amaranthus | Mustard |
|---|---|---|---|---|---|---|---|---|---|---|---|---|
| $H_3CCO$ / Cl-phenyl cyclohexanedione | λmax (μ); 5.70 (ester C=O); 6.00, 6.08 (keto C=O) | C | A | 2 | 5 | 2 | 1 | 2 | 5 | 4 | 1 | 3 |
| $H_3C-(H_2C)_4-CO$ / Cl-phenyl cyclohexanedione | λmax (μ); 5.70 (ester C=O); 6.00 6.05 (keto C=O) | A | A | 3 | 5 | 2 | 2 | 2 | 5 | 5 | 1 | 1 |
| $H_3C-(H_2C)_3-C(CH_2CH_3)-CO$ / Cl-phenyl cyclohexanedione | λMax (μ); 5.72 (ester C=O); 6.00 6.10 (keto C=O) | A | A | 2 | 5 | 1 | 1 | 2 | 3 | 4 | 1 | 1 |
| $H_3C-(H_2C)_{16}-CO$ / Cl-phenyl cyclohexanedione | λMax (μ); 5.72 (ester C=O); 6.00, 6.10 (keto C=O) | C | A | 2 | 3 | 1 | 1 | 1 | 4 | 4 | 1 | 1 |
| $H_3C-(H_2C)_4-CO$ / 2,4-diCl-phenyl cyclohexanedione | λmax (μ); 5.70 (ester C=O), 5.98, 6.08 (keto C=O) | A | A | 2 | 3 | 1 | 2 | 3 | 5 | 5 | 1 | 1 |
| $(H_3C)_2HCCO$ / CH$_3$-phenyl cyclohexanedione | λmax (μ): 5.73 (ester C=O), 6.03 6.12 (keto C=O) | A | A | 2 | 5 | 2 | 2 | 2 | 5 | 5 | 1 | 1 |
| $H_3C-(H_2C)_4-CO$ / CH$_3$-phenyl cyclohexanedione | λmax (μ); 5.70 (ester C=O), 6.00 6.08 (keto C=O) | A | B | 2 | 5 | 2 | 2 | 2 | 5 | 5 | 1 | 1 |

TABLE I-continued
PHYSICAL PROPERTIES AND BIOLOGICAL ACTIVITY OF 2-ARYL-1,3-CYCLOHEXANEDIONE ENOL ESTER COMPOUNDS
| STRUCTURE | MP °C. or IR | Miticidal | | Post-emergent Herbicidal | | | | | Pre-emergent Herbicidal | | | |
|---|---|---|---|---|---|---|---|---|---|---|---|---|
| | | Adult | Egg | Bean | Corn | Tomato | Cotton | Soybean | Rye | Crabgrass | Amaranthus | Mustard |
| 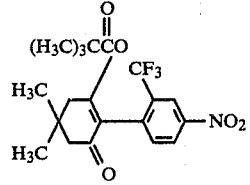 | 106–107 | C | C | 1 | 1 | 1 | 1 | 1 | 1 | 1 | 1 | 1 |
| 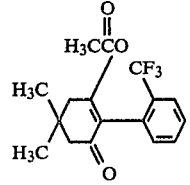 | 92.0–92.5 | C | C | 2 | 3 | 2 | 2 | 2 | 5 | 5 | 1 | 2 |
| 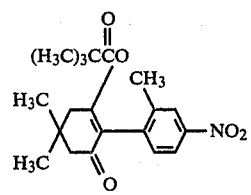 | 93–96 | A | A | 1 | 1 | 1 | 1 | 1 | 1 | 1 | 1 | 1 |
| 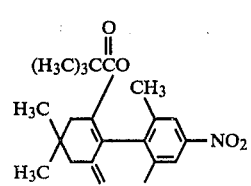 | 120–121 | C | C | 1 | 1 | 1 | 1 | 1 | 1 | 1 | 1 | 1 |
| 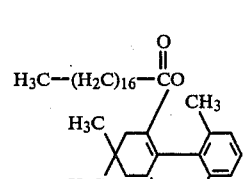 | 62–63 | A | A | 1 | 1 | 1 | 1 | 1 | 1 | 1 | 1 | 1 |
| 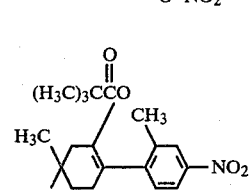 | 103–106 | A | A | 1 | 1 | 1 | 1 | 1 | 1 | 1 | 1 | 1 |
| 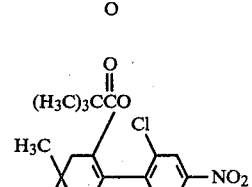 | 111–112 | C | C | 1 | 1 | 1 | 2 | 2 | 1 | 1 | 1 | 1 |

TABLE I-continued

PHYSICAL PROPERTIES AND BIOLOGICAL ACTIVITY OF 2-ARYL-1,3-CYCLOHEXANEDIONE ENOL ESTER COMPOUNDS

| STRUCTURE | MP °C. or IR | BIOLOGICAL ACTIVITY | | | | | | | | | |
|---|---|---|---|---|---|---|---|---|---|---|---|
| | | Miticidal | | Post-emergent Herbicidal | | | | | Pre-emergent Herbicidal | | |
| | | Adult | Egg | Bean | Corn | Tomato | Cotton | Soybean | Rye | Crabgrass | Amaranthus | Mustard |
| (structure with (H$_3$C)$_3$CCO, H$_3$C, H$_3$C, Cl, NO$_2$) | 65–68 | A | A | 2 | 1 | 2 | 1 | 2 | 1 | 1 | 1 | 1 |
| (structure with H$_3$C—(H$_2$C)$_{16}$—CO, H$_3$C, H$_3$C, Cl, Cl, NO$_2$) | 44–45 | B | C | 1 | 1 | 1 | 1 | 1 | 1 | 1 | 1 | 1 |
| (structure with (H$_3$C)$_2$HCCO, CH$_3$) | λmax. (μ); 5.75 (ester C=O) 6.03, 6.12 (keto C=O) | A | A | 2 | 5 | 2 | 2 | 2 | 5 | 5 | 1 | 1 |
| (structure with H$_3$C(H$_2$C)$_4$—CO, CH$_3$) | λmax (μ); 5.70 (ester C=O) 6.00, 6.08 (keto C=O) | A | A | 2 | 5 | 2 | 2 | 2 | 5 | 5 | 1 | 1 |
| (structure with H$_3$CH$_2$C, H$_3$C—(CH$_2$)$_3$—CH—CO, Cl, Cl) | λmax (μ); 5.70 (ester C=O) 5.98, 6.08 (keto C=O) | A | A | 2 | 3 | 1 | 1 | 2 | 1 | 1 | 1 | 1 |
| (structure with H$_3$C—(H$_2$C)$_{16}$—CO, Cl, Cl) | 34.0–34.5 | A | A | 1 | 3 | 1 | 1 | 1 | 5 | 2 | 1 | 1 |
| (structure with CH$_3$CH$_2$, H$_3$C—(H$_2$C)$_4$—HC—CO, CH$_3$, CH$_3$) | λmax (μ); 5.75 (ester C=O) 6.00, 6.10 (keto C=O) | A | A | 1 | 5 | 1 | 1 | 2 | 5 | 3 | 1 | 1 |

TABLE I-continued

PHYSICAL PROPERTIES AND BIOLOGICAL ACTIVITY OF 2-ARYL-1,3-CYCLOHEXANEDIONE ENOL ESTER COMPOUNDS

| STRUCTURE | MP °C. or IR | BIOLOGICAL ACTIVITY | | | | | | | | | |
|---|---|---|---|---|---|---|---|---|---|---|---|
| | | Miticidal | | Post-emergent Herbicidal | | | | | Pre-emergent Herbicidal | | | |
| | | Adult | Egg | Bean | Corn | Tomato | Cotton | Soybean | Rye | Crabgrass | Amaranthus | Mustard |
| H₃C—(H₂C)₁₆—CO— [2-aryl-1,3-cyclohexanedione with 2,4-dimethylphenyl] | λmax (μ); 5.75 (ester C=O) 6.00, 6.15 (keto C=O) | A | A | 1 | 3 | 1 | 1 | 1 | 5 | 5 | 1 | 1 |
| H₃C—(H₂C)₃—HC(CH₂CH₃)—CO— [5,5-dimethyl-2-(2,4-dimethylphenyl)] | λmax (μ); 5.78 (ester C=O) 6.05, 6.15 (keto C=O) | A | A | 1 | 5 | 1 | 1 | 1 | 5 | 1 | 1 | 1 |
| H₃C—(H₂C)₃—HC(CH₂CH₃)—CO— [5,5-dimethyl-2-(2,5-dichloro-4-methylphenyl)] | λmax (μ); 5.78 (ester C=O) 6.05, 6.10 (keto C=O) | A | A | 1 | 1 | 2 | 1 | 2 | 1 | 1 | 1 | 1 |
| H₃C(H₂C)₄—CO— [5,5-dimethyl-2-(2,5-dimethylphenyl)] | λmax (μ); 5.75 (ester C=O) 6.0, 6.05 (keto C=O) | A | A | 2 | 4 | 2 | 2 | 2 | 5 | 4 | 1 | 1 |
| H₃C—(H₂C)₃—HC(CH₂CH₃)—CO— [5,5-dimethyl-2-(2,5-dimethylphenyl)] | λmax (μ); 5.75 (ester C=O) 6.05, 6.10 (keto C=O) | A | A | 1 | 2 | 1 | 1 | 2 | 1 | 1 | 1 | 1 |
| H₃CCO— [5,5-dimethyl-2-(2-methylphenyl)] | λmax (μ); 5.70 (ester C=O) 6.00, 6.05 (keto C=O) | A | A | 2 | 5 | 1 | 2 | 2 | 5 | 5 | 3 | 3 |
| (H₂C)₂HCCO— [5,5-dimethyl-2-(2-methylphenyl)] | 77–78 | A | A | 2 | 5 | 1 | 2 | 2 | 5 | 5 | 3 | 3 |

TABLE I-continued
PHYSICAL PROPERTIES AND BIOLOGICAL ACTIVITY OF 2-ARYL-1,3-CYCLOHEXANEDIONE ENOL ESTER COMPOUNDS

| STRUCTURE | MP °C. or IR | Miticidal | | Post-emergent Herbicidal | | | | | Pre-emergent Herbicidal | | | |
|---|---|---|---|---|---|---|---|---|---|---|---|---|
| | | Adult | Egg | Bean | Corn | Tomato | Cotton | Soybean | Rye | Crabgrass | Amaranthus | Mustard |
| 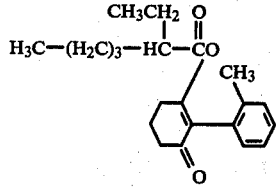 | λmax (μ); 5.78 (ester C=O) 6.00, 6.10 (keto C=O) | A | A | 2 | 5 | 2 | 1 | 3 | 2 | 1 | 1 | 1 |
| 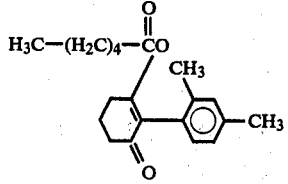 | λmax (μ); 5.73 (ester C=O) 6.00, 6.10 (keto C=O) | A | A | 2 | 4 | 2 | 2 | 2 | 5 | 5 | 2 | 2 |
| 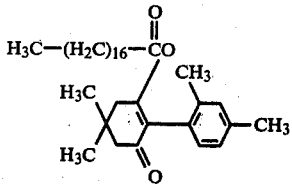 | λmax (μ); 5.75 (ester C=O) 6.05, 6.10 (keto C=O) | A | A | 2 | 3 | 2 | 2 | 2 | 5 | 3 | 1 | 1 |
| 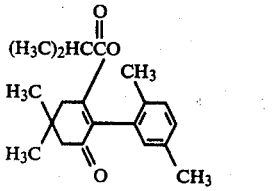 | λmax (μ); 5.80 (ester C=O) 6.10, 6.15 (keto C=O) | A | B | 2 | 4 | 1 | 2 | 3 | 5 | 5 | 1 | 2 |
| 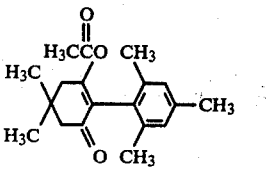 | 110–111 | A | A | 1 | 1 | 1 | 1 | 2 | 5 | 5 | 4 | 3 |
| 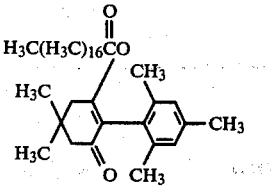 | 29–30 | A | A | 1 | 1 | 1 | 1 | 1 | 5 | 5 | 2 | 1 |
| 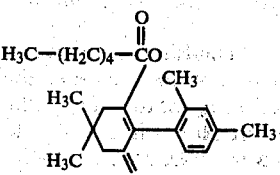 | λmax (μ); 5.78 (ester C=O) 6.05, 6.15 (keto C=O) | A | A | 2 | 5 | 2 | 2 | 2 | 5 | 5 | 4 | 5 |

TABLE I-continued
PHYSICAL PROPERTIES AND BIOLOGICAL ACTIVITY OF 2-ARYL-1,3-CYCLOHEXANEDIONE ENOL ESTER COMPOUNDS

| STRUCTURE | MP °C. or IR | Miticidal | | Post-emergent Herbicidal | | | | | Pre-emergent Herbicidal | | | |
|---|---|---|---|---|---|---|---|---|---|---|---|---|
| | | Adult | Egg | Bean | Corn | Tomato | Cotton | Soybean | Rye | Crabgrass | Amaranthus | Mustard |
| (structure) | 79-84 | A | A | 2 | 1 | 1 | 2 | 2 | 5 | 5 | 2 | 2 |
| (structure) | 132-133 | C | A | 1 | 1 | 1 | 1 | 1 | 3 | 3 | 1 | 1 |
| (structure) | 111-113 | C | C | 1 | 1 | 1 | 1 | 1 | 5 | 5 | 1 | 1 |
| (structure) | 38-40 | A | A | 1 | 2 | 2 | 1 | 1 | 5 | 3 | 1 | 1 |
| (structure) | 71-73 | B | B | 1 | 4 | 3 | 1 | 2 | 5 | 5 | 1 | 1 |
| (structure) | 61-62 | A | A | 1 | 1 | 1 | 1 | 2 | 5 | 4 | 1 | 1 |

It will be understood that the plant species employed in the above tests are merely representative of a wide variety of plant pest that can be controlled by the use of the compounds of this invention. The compounds contemplated in this invention may be applied as mite ovicides, miticides and pre-emergent herbicides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agents as is possible, consistent with the desired dispersion of the toxicant in the spray so that rain does not re-emulsify the toxicant after it is applied to the plant and wash it off the plant. Nonionic, anionic, amphoteric or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultra violet light, oxidation, or hydrolysis in the presence of moisture or, at least such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are compatible with substantially any other constituents of the spray schedule, and they may be used in the soil, upon the seeds, or the roots of plants without injuring either the seeds or roots of plants. They may also be used in combination with other pesticidally active compounds. When used as miticides they will normally be applied to the foliage of the plants to be treated. When used as herbicides they may be used in the soil or directly upon the seeds to be treated. The compounds of this invention may also be used in combination with other pesticidally active materials.

What is claimed is:
1. 3-(2-Ethylhexanoyloxy)-5,5-dimethyl-2-(2',4'-dimethylphenyl)-2-cyclohexenone.
2. 3-(2-Ethylhexanoyloxy)-5,5-dimethyl-2-(2',5'-dimethylphenyl)-2-cyclohexenone.
3. 3-(2-Ethylhexanoyloxy)-5,5-dimethyl-2-(2',4'-dichlorophenyl)-2-cyclohexenone.
4. 3-(2-Ethylhexanoyloxy)-5,5-dimethyl-2-(2'-methylphenyl)-2-cyclohexenone.
5. 3-(2-Ethylhexanoyloxy)-5,5-dimethyl-2-(2'-chlorophenyl)-2-cyclohexenone.
6. A miticidal, mite ovicidal or herbicidal composition comprising an acceptable carrier and as the active toxicant a miticidally, mite ovicidally or herbicidally effective amount of 3-(2-ethylhexanoyloxy)-5,5-dimethyl-2-(2',4'-dimethylphenyl)-2-cyclohexenone.
7. A miticidal, mite ovicidal or herbicidal composition comprising an acceptable carrier and as the active toxicant a miticidally, mite ovicidally or herbicidally effective amount of 3-(2-ethylhexanoyloxy)-5,5-dimethyl-2-(2',5'-dimethylphenyl)-2-cyclohexenone.
8. A miticidal, mite ovicidal or herbicidal composition comprising an acceptable carrier and as the active toxicant a miticidally, mite ovicidally or herbicidally effective amount of 3-(2-ethylhexanoyloxy)-5,5-dimethyl-2-(2',4'-dichlorophenyl)-2-cyclohexenone.
9. A miticidal, mite ovicidal or herbicidal composition comprising an acceptable carrier and as the active toxicant a miticidally, mite ovicidally or herbicidally effective amount of 3-(2-ethylhexanoyloxy)-5,5-dimethyl-5,5-dimethyl-2-(2'-methylphenyl)-2-cyclohexenone.
10. A miticidal, mite ovicidal or herbicidal composition comprising an acceptable carrier and as the active toxicant a miticidally, mite ovicidally or herbicidally effective amount of 3-(2-ethylhexanoyloxy)-5,5-dimethyl-2-(2'-chlorophenyl)-2-cyclohexenone.

* * * * *